(12) United States Patent
Zhu et al.

(10) Patent No.: US 8,111,151 B2
(45) Date of Patent: Feb. 7, 2012

(54) WAN-BASED REMOTE MOBILE MONITORING METHOD AND DEVICE OF ELECTROPHYSIOLOGICAL DATA

(76) Inventors: Xiaohong Zhu, Beijing (CN); Haiqing Gao, Beijing (CN); Yonggang Zhao, Beijing (CN); Qichun Chen, Beijing (CN); Shiang Sun, Beijing (CN)

( * ) Notice: Subject to any disclaimer, the term of this patent is extended or adjusted under 35 U.S.C. 154(b) by 368 days.

(21) Appl. No.: 12/087,725

(22) PCT Filed: Jan. 15, 2007

(86) PCT No.: PCT/CN2007/000136
§ 371 (c)(1),
(2), (4) Date: Jul. 14, 2008

(87) PCT Pub. No.: WO2007/082462
PCT Pub. Date: Jul. 26, 2007

(65) Prior Publication Data
US 2010/0240980 A1 Sep. 23, 2010

(30) Foreign Application Priority Data
Jan. 17, 2006 (CN) .......................... 2006 1 0000895

(51) Int. Cl.
*G08B 1/00* (2006.01)
(52) U.S. Cl. ....... 340/539.12; 702/19; 702/22; 600/300; 600/301; 600/481; 455/552.1; 455/553.1; 455/423
(58) Field of Classification Search ............. 340/539.12; 702/19, 22; 600/300, 301, 481; 455/552.1, 455/553.1, 423
See application file for complete search history.

(56) References Cited

U.S. PATENT DOCUMENTS

| | | | |
|---|---|---|---|
| 6,057,758 A * | 5/2000 | Dempsey et al. | 340/539.12 |
| 7,110,747 B2 * | 9/2006 | Jain et al. | 455/411 |
| 7,188,151 B2 * | 3/2007 | Kumar et al. | 709/217 |
| 7,616,110 B2 * | 11/2009 | Crump et al. | 340/539.11 |
| 2005/0080322 A1 * | 4/2005 | Korman | 600/300 |
| 2005/0154323 A1 * | 7/2005 | Vogtmeier et al. | 600/509 |
| 2005/0206518 A1 * | 9/2005 | Welch et al. | 340/539.12 |
| 2005/0226201 A1 * | 10/2005 | McMillin | 370/348 |
| 2008/0310611 A1 * | 12/2008 | Moriwaki et al. | 379/212.01 |
| 2009/0231125 A1 * | 9/2009 | Baldus et al. | 340/539.12 |
| 2010/0076333 A9 * | 3/2010 | Burton et al. | 600/544 |

* cited by examiner

Primary Examiner — Kamran Afshar
Assistant Examiner — Yousef Rod
(74) Attorney, Agent, or Firm — CBM Patent Consulting (57) ABSTRACT

A WAN-based remote mobile monitoring method and device of electrophysiological data, including microprocessor circuit, electrophysiological signal sampling processing circuit, data storage circuit, image liquid crystal circuit, real-time clock, emergent calling circuit, working power supply management circuit, wireless network interface circuit, USB interface circuit, etc, has the in-built binding IP address of the remote electrophysiological data monitoring server, TCP/IP protocol, PPP protocol and BlueTooth protocol. Application controls self-adaptive analysis computing, exception event warning and alarming privilege graded setting, event data package combination, network digital communication, data storage circuit area management, safety information data storage management and remote emergent calling of the remote mobile monitoring devices. It can have access to Internet in motion and roaming access to Internet by internetwork switch, and have access to the exterior networks wirelessly including Internet, LAN, ADSL, VDSL, ISDN, etc, for digital communication with the remote electrophysiological data monitoring server.

11 Claims, 8 Drawing Sheets

WAN-BASED REMOTE MOBILE MONITORING METHOD AND DEVICE OF ELECTROPHYSIOLOGICAL DATA

TECHNICAL FIELD OF THE INVENTION

This invention belongs to medical care information processing tool for individual use. It is a WAN-based remote mobile monitoring method and device of electrophysiological data.

BACKGROUND OF THE INVENTION

Most victims suffering cardiovascular disease (coronary heart disease, high blood pressure) lose their lives in a sudden emergent event owing to missing the good time for earlier cure. Electrophysiological parameters of a patient such as ECG and blood pressure are already premonitory disorder before emergent event. If these exception symptoms of patients are discovered earlier and patients are cured in time, their lives will be saved. The telephone transmission ECG remote monitoring system were invented successfully for simulating frequency modulation with U.S. Pat. No. 4,635,646 in 80s. If a patient feels any discomfort, he/she can transmit an electrocardiogram to the receiving scanning system of hospital by fixed telephone for analysis from a duty doctor. The technology which could transmit remote monitoring with the digital telephone interconnecting network was invented with China patent 91102750.5 in 90s. It has functions of real-time analysis forewarning and storage and process user monitoring data using computer workstation. The main function of this technology is that the exception ECG premonitory syndromes of patients can be found earlier to give cure in time, so it lowers death rate and disabled rate and has abundant clinical data and clinical experience.

In recent years, the technology of applying data mobile communication network for ECG remote monitoring has been invented with U.S. Pat. Nos. 6,801,137, 6,665,385. The heart monitoring of user terminal is divided into two units when using this technology. One unit is the ECG signal sampling terminal, which is used for filter sampling and modulus conversion of ECG signal. The other unit is digital mobile telephone with PDA or a monitor with digital mobile phone module, which is used for monitoring data analysis storage and digital communication. The two units are interconnected by the wireless receiving and sending modulus RF6900 to realize ECG remote mobile monitoring. But there are disadvantages in the existing technologies above:

1 For the existing ECG remote monitoring technology transmitted by telephone, a user must find available fixed telephone to call the fixed telephone of the receiving terminal. It can only been transmitted after receiving answer. Only one user is online at the same time and other users can continue to call for transmission when the line is in leisure. So it can not meet requirements of emergent event heart monitoring.

2 For the existing technology applying digital mobile communication network remote monitoring, it can only use GPRS or CDMA. Wherein one digital mobile communication network can not be compatible with different modulation digital mobile communication networks, can not use 3G digital mobile communication network and meanwhile can not access to other exterior network for digital communication.

3 The existing technologies with U.S. Pat. Nos. 6,665,385, 6,694,177 apply fixed telephone network or wireless calling network and satellite communication network as backup data channel of remote monitoring. The disadvantages of fixed telephone are discussed above. The wireless calling network can not transmit ECG images but some compressed simplified data owing to technology mode limiting. Satellite communication network is expensive and needs different data receiving and sending devices. For other technologies, data are transmitted into PC by USB interface of PDA and login in Internet for transmitting these data. These existing technologies are not convenient.

4 The existing technology divides ECG sampling and analysis storage of user terminal into two units which are interconnected by RF6900 wirelessly. FR6900 is a kind of low-level wireless communication mode, which is generally used in different kinds of industry and appliances. The working frequency of RF6900 is 900 MHz. It only has one hopping frequency channel without the function of addressing wireless communication, so it can not be unique and it can solve the problem of conflict in the same frequency or devices in the congestion condition of 900 MHz. In recent period, apply the technology of 2.4 GHz Bluetooth to substitute RF6900 for solving this problem, such as China patent 03116539.7, but it is large-power consumption in working state of Bluetooth. Data and real-time monitoring analysis can not been transmitted continuously for long time between two units. Meanwhile the user client is divided into two units so it is not convenient.

5 For the existing technology with U.S. Pat. No. 66,941,177, the user terminal only transmits a little of monitoring data first under whatever conditions. The center system judges whether the main body is needed to monitoring according to these data and notify the user terminal to transmit the monitoring data body needed for clinic diagnosis, so it saves communication time and expense. As the technology of digital mobile communication develops, network broadband and speed are increased largely to lower the mobile phone consumption and cost. This kind of data structure mode and graded transmission mode falls behind evidently, and it can not meet the requirement of quick analysis and diagnosis of emergent heart event.

6 The existing technology has no function of safety information data management. It can not supply law and medical evidence for the likelihood of medical care dispute and meanwhile lack the function of remote calling help under non-monitoring state.

7 The existing technology is no international unified benchmark calibration voltage for ECG data analysis computing. It has large deviation for ST quantification computing of acute myocardial infarction, acute myocardial ischemia and silent myocardial ischemia diagnosis. Automatic gain control circuit supplies calibration voltage signal for China patent 91102750.5, but ECG signal will generate deviation in the critical value or when benchmark line fluctuates.

SUMMARY OF THE INVENTION

For compensating the above disadvantages of the existing technology, the purpose of this technology is to supply a remote mobile monitoring method and device of electrophysiological data connecting to WAN which is simply, portable and can access to the exterior network terminal interface. And it can achieve functions of real-time electrophysiological data monitoring, record storage, self-adaptive analysis forewarning, network digital communication and emergent remote calling, and achieve network connection in motion and by inter-network roaming switch, and exchange data information with exterior network devices to meet requirements of electrophysiological data remote mobile monitoring of uses in public places and houses.

The technology solution of this invention is: a WAN-based remote mobile monitoring method and device of electrophysiological data which features that it is comprised of microprocessor circuit, electrophysiological signal sampling processing circuit, data storage circuit, image liquid crystal circuit, real-time clock circuit, emergent calling circuit, working power supply management circuit, wireless network interface circuit, mechanical vibrant circuit, buzzer circuit, USB interface circuit and which has in-built TCP/IP protocol, PPP protocol and BlueTooth protocol. The microprocessor circuit controls different functional modulus circuits to realize remote mobile monitoring electrophysiological data and network digital communication; electrophysiological signal sampling circuit is used to sample electrocardio, blood pressure and breath simulating signal and supplies benchmark calibration voltage for self-adaptive analysis computing; data storage circuit is divided into five data storage areas in control of microprocessor circuit which respectively store different kinds of data remote mobile monitoring devices as stated, including fixed IP,SP code, data mobile telephone number, MMS address and help information of remote electrophysiological data monitoring server by user setting; image liquid crystal circuit shows electrophysiological signal waveform, image symbols and different kinds of words in control of microprocessor circuit, and has glint light as forewarning; real-time clock circuit supplies calendar and real time 24-hour clock for application; emergent calling circuit sends emergent calling triggering command to microprocessor circuit and controls the wireless network interface circuit to send help information to the predetermined receiving terminal; mechanical vibrant circuit and buzzer circuit supplies vibration and sound as alarming in control of microprocessor circuit; working power supply circuit supplies electricity for different module circuits in control of microprocessor circuit; USB circuit is connected to the USB interface of exterior circuit, which is used to exchange data information and transmit and download electrophysiological data of continuous monitoring record in control of microprocessor circuit; wireless network circuit can access to the exterior network terminal interface wirelessly to connect WAN and achieve network digital communication in control of microprocessor circuit. The exterior network terminal interface as stated in this invention includes but is not limited to mobile Internet, LAN, ADSL, VDSL, ISDN, DDN, CATV communication network and electric power communication terminal interface.

This invention presents a WAN-based remote mobile monitoring method of electrophysiological data including application running in remote mobile monitoring devices, which has following steps:

Self-adapting analysis computing step for application as sated for controlling the remote mobile monitoring devices as stated;

Step for exception event caution and alarm privilege grade setting;

Step for combination of event data packages and network digital communication;

Step for data storage circuit area management and safety information data storage management;

Step for remote emergent calling;

Wherein, application as stated which controls the remote mobile monitoring device as stated accesses to the exterior network terminal interface to connect WAN for network digital communication, network connection in motion and by inter-network roaming switch. The exterior network terminal interface includes but is not limited to mobile Internet, LAN, ADS, VDSL, ISDN, DDN, CATV communication network and power electricity line communication network terminal interface.

A WAN-based remote mobile monitoring method of electrophysiological data as stated includes the following steps:

step1: application as stated computes the current electrophysiological data according to the calibration voltage and gain sampling to obtain the initial data. If application determines that the initial data is in the setting range of threshold value, it is used as the initial value of this monitoring to start monitoring analysis computing. If the initial value reaches to the setting threshold value, application as stated will set the initial value flag and store it. Set the upper limit or lower limit self-adaptively. This initial value is used as the initial value of this monitoring to start monitoring analysis computing. When the monitoring data reaches to the self-adaptive threshold value, application as stated will set the exception electrophysiological event flag and send data flag. If the initial value exceeds the setting threshold value, application as stated will set the exception electrophysiological event flag and send data flag.

step2: application as stated sets different level alarm flags according to different kinds of exception event flags as stated and set the forewarning privilege of remote mobile monitoring devices as stated including first-level warning privilege, second-level warning privilege and third-level warning privilege. When the warning flag as stated is set, the relative command circuit performs the operation of alarming or forewarning.

step3: application as stated arranges forward 6 sixty-minute intervals and obtains event data records relating to this event in the 6 intervals to compose an event data package by time sequence. When the number of intervals is less than 6, get the maximum time.

step4: application as stated commands the wireless network interface circuit to power on according to the sending data flag. Use the BlueTooth protocol to send the searching command. After the exterior network terminal interface responses in valid distance, the wireless network interface circuit sends an individual identity address code Pin to check match. Build wireless dual-direction digital communication link. Application as stated sends the recognition command to judge whether the exterior network is mobile Internet or cable network.

step5: if application as stated determines that the exterior network is mobile Internet, then read the fixed IP address of remote electrophysiological data monitoring server and call TCP/IP protocol and PPP protocol. If it is cable network, application as stated reads the fixed IP address of remote electrophysiological data monitoring server, calls the cable network control command, controls the wireless network interface circuit to connect the mobile Internet or cable network, performs network digital communication with remote electrophysiological data monitoring server, sends event data packages or data information, receives the control command, analysis result and processing notes sent from the server and responses to execute the control command.

step6: application as stated controls wireless network interface circuit to enter into the online connection holding state (Hold). Stop data transmission and hold online connection. When application as stated or remote electrophysiological data monitoring server send activation signal, recover digital communication immediately.

step7: data memory circuit as stated is divided into word base storage area, setting information storage area, safety information storage area, exception electrophysiological data storage area, continuous electrophysiological data storage area according to application addressing as stated. Execute the operation of reading, writing, modification and cancellation according to the corresponding areas of the application commands and addressed as sated. Set the safe information storage area for cyclic record storage which can not been cancelled artificially and the cyclic record period can be set with flexibility.

step8: when application as stated receives setting information data from the remote mobile monitoring devices as stated, it will send the writing command to the data storage circuit and set address for data to store it in the setting information storage area.

step9: when application as stated receives operating information data from the remote mobile monitoring devices as stated, it will send the writing command to the data storage circuit and set address for data to store it in the sate information storage area.

Step10: when application as stated receives emergent calling triggering signal, set the emergent calling flag and send data flag. Read SP code digital mobile phone number or MMS address and help information, control the wireless network interface circuit to connect the SMSC of mobile network terminal interface and send help information to the predetermined receiving terminal. If application as stated does not receive "receive" information returned from the receiving terminal, read the fixed IP address and help information of the binding remote electrophysiological data monitoring server, control the wireless network interface circuit to access WAN, send help information to the remote electrophysiological data monitoring server, receive the "receive" information returned from the receiving terminal and terminate cyclic calling.

This invention has the following technology features compared to the existing technology:

1 This invention supplies a remote mobile monitoring method of electrophysiological data connected to the exterior network wirelessly. A user can access to WAN by the exterior network terminal interface wirelessly nearby and achieve network digital communication with remote devices. The exterior network terminal interface includes but is not limited to mobile Internet (CDMA, GPRS, 3G, etc), LAN, VDSL, ISDN, DDN, CATV communication network, electricity power communication network terminal interface and can realize network connection in motion and by inter-network roaming switch, so it compensates disadvantages in the existing technology and extends new application.

2 This invention independently achieves functions of monitoring analysis of electrophysiological data, storage forewarning and network digital communication, compensates disadvantages in the existing "Split-type" technology, meanwhile supplies a method for event data package time sequence combination, selects the recent event data record related to this event to compose data package automatically. So it avoids the possibility of multi-transmission back and forth, improves monitoring working efficiency and lower cost.

3 This inventor supplies a graded setting method of exception event warning and alarming privilege. The remote mobile monitoring devices as stated only have forewarning privilege to pathologic exception event and sends pathologic exception event alarming to reduce error alarming when receiving the command sent from the server.

4 This invention supplies a data storage area management method. The safety information storage area stores operating information of remote mobile monitoring devices as stated. Information can not been cancelled artificially and stored cyclically to supply law and medical evidence for the likelihood of medical care dispute, so it extends the function and application of data storage circuit.

5 This invention supplies a remote emergent calling method. When a user feels any discomfort in non-monitoring state, he/she can send help information via the exterior network terminal interface by triggering emergent calling.

6 This invention supplies a circuit generating calibration voltage signal, assures accuracy of electrophysiological data analyzed and computed by software program and supplies benchmark for analysis and computing by remote monitoring server of electrophysiological data and doctors.

7 This inventor has the feature of low-consumption, can be 48-hour continuous working time using 3.7V800 mA lithium battery and is suitable for individual use due to its small volume and simply operation.

DETAILED DESCRIPTION OF THE PREFERRED EMBODIMENTS

Describe further this invention with attached images and examples.

Example 1

Figure 1:
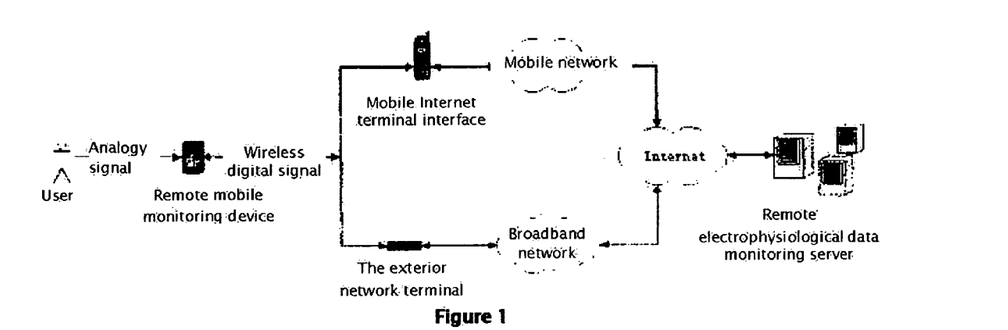
FIG. 1, topology figure for WAN-based electrophysiological data remote mobile monitoring network.
Figure 2:
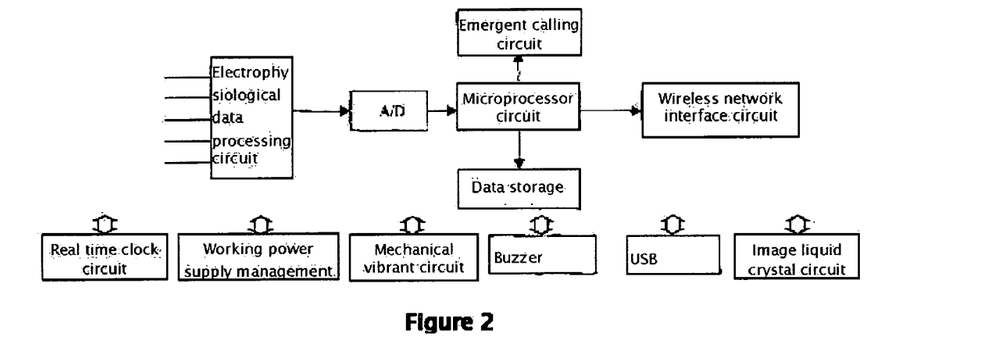
FIG. 2, principle frame figure for WAN-based electrophysiological data remote mobile monitoring devices.
Figure 3:
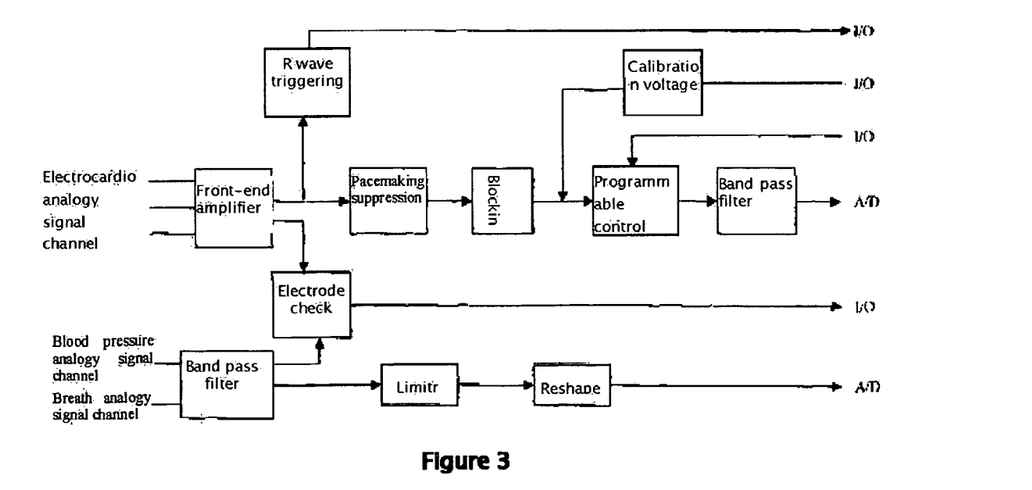
FIG. 3, principle frame figure for electrophysiological data sampling processing circuit.
Figure 4:
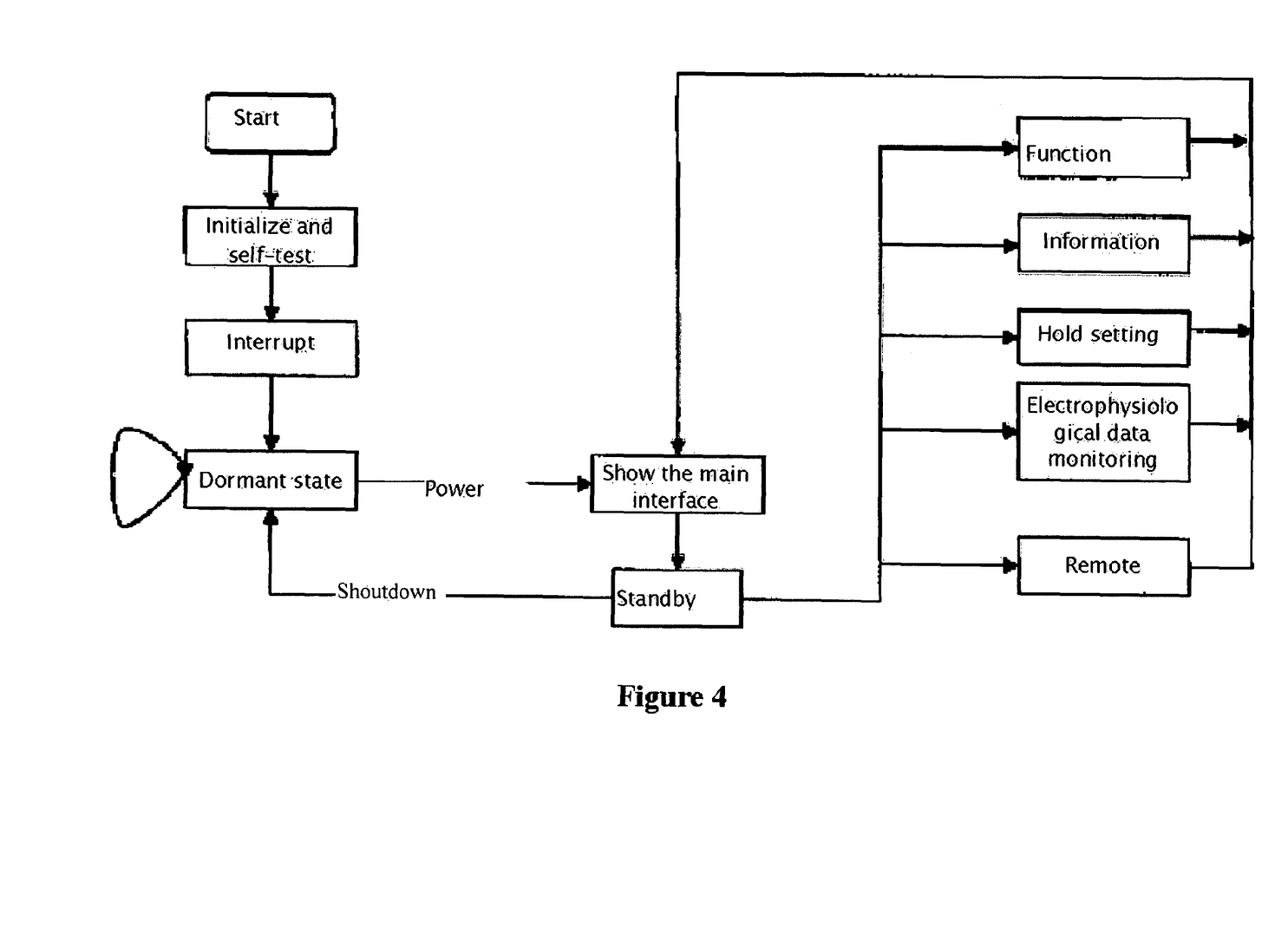
FIG. 4, flow chart for main program.

The hardware working principle refers to FIGS. 1, 2 and 3. This invention is comprised of microprocessor circuit, electrophysiological signal, sampling processing circuit, data storage circuit, image liquid crystal circuit, real-time clock circuit, emergency, working power supply management circuit, wireless network interface circuit, mechanical vibrant circuit, buzzer circuit and USB interface circuit, which has in-built binding fixed IP address, TCP/IP protocol, PPP protocol and BlueTooth protocol.

The microprocessor circuit is comprised of low-consumption monolithic processor. The monolithic processor can be M30280 with 10-bit A/D modulus converter and 100KFlashROM inside which connects I/O port, exterior interruption source, serial communication port and internal A/D analog converter to different functional modules respectively; install application into FlashROM. The monolithic processor can be M30281 or HD64F3847 whose pins are connected by the labels.

The 1-3 channels of electrophysiological signal sampling processing circuit is a synchronization three-lead ECG channel. Each channel is comprised of common front-end amplification circuit, pacing pulse suppressing circuit, blocking circuit, programmable-controlled gain amplifier and band pass filter circuit in sequence, and has common sensor dropping check circuit, R wave triggering circuit and special calibration voltage signal circuit. Three inputs of sensor dropping check circuit are connected to input of the front-end circuit of three channels. The input of R wave triggering circuit is connected to input of the front-end circuit of the third channel. The output of calibration voltage signal circuit is connected to output of blocking circuit of three channels respectively. The output of band pass filter circuit of three channels is connected to output of P10.2-P10.4 of A/D modulus converter inside microprocessor circuit M30280. The control ends A and B of programmable control gain amplifier are connected to P1.0-P1.1 of P1 port of microprocessor circuit M30280 respectively. The outputs of sensor dropping check circuit and R wave triggering circuit are connected to the interruption port 1 and 2 of microprocessor circuit M30280 respectively. The 4 and 5 channels are the channel of blood pressure signal sampling and the channel of breath signal sampling respectively. Each channel is comprised of common band pass filter circuit, limitr circuit, reshaper circuit connected in sequence. The outputs of reshaper circuit of two channels are connected to outputs of P10.5-P10.6 of A/D modulus converter inside microprocessor circuit M30280 respectively.

The calibration voltage signal circuit inside the electrophysiological signal sampling circuit is comprised of precision benchmark resource, triode 9013, current limiting resistor and precision voltage division resistor. The precision benchmark resource can be NJM2823. The base pole of triode 9013 is connected to P1.2 of P1 port of microprocessor circuit M30280, the emitter is connected to +3.3V power supply end of the main circuit, and the collector is connected to ground and the negative electrode of NJM2823 via two current limiting resistors. The positive electrode is connected to ground. Two precision voltage resistors are in series. One end is connected to the negative electrode of NJM2823, one end is connected to ground and the middle end is connected to the output of blocking circuit. The range of the output of calibration voltage is 1 mv×front-end amplifier times. Deviation is less than ±1%. The precision benchmark resource can be CYT431, TL431B or LM4050 whose pins are connected by labels.

Data storage circuit is comprised of microprocessor circuit M30280 and data memory Flash. Data memory Flash can be NAND01G. P0.0-P0.7 of P0 of microprocessor circuit M30280 are connected to the data lines D0-D7 of NAND01G respectively. P2.2-P2.4 of P2 port of M30280 are connected to chip selection end E, address locking end AL and command locking end CL of NAND01G respectively. P3.4-P3.5 of P3 port of M30280 are connected to the reading end RD and writing end WR of NAND01G. Data memory Flash can be RC28F13C-150, TC58DVG02A1 FT00 or K9K1 GU0B whose pins are connected by labels.

The emergent circuit is comprised of key triggering circuit and microprocessor M30280. The input of key triggering circuit is connected to the +3.3V power supply end of the main circuit and the output is connected to the interruption source 3 of P1 port of M30280 and is connected to ground via a pull-down resistor.

Wireless network interface circuit is comprised of microprocessor circuit M30280, network processor circuit IP2022 and BlueTooth integrated circuit. BlueTooth integrated circuit can be BlueCore313143. TXD, RXD, CTS, DSR of the serial communication port 0 of microprocessor circuit are connected to the serial communication port 1 of IP2022. P5.0-P5.2 of P5 port of M30280 are connected to the reset end RST, state control end PRG and sleeping control end ON/OFF of IP2022 respectively. HOST_TX, HOST_RX, HOST_CTS and HOST_RTS of serial communication port 2 of IP2022 are connected to UART_RX, UART_TX, UART_RTS and UART_CTS of BlueCore313143 respectively. PORTSEL, SLEEP_ENABLE, HOST_INT and DISCONNECT of IP2022 are connected to the reset end RESET, power supply end VREG_EN, wakeup end PWR_UP and disconnection end DISCONNECT_CON of BlueCore313143 respectively. BlueTooth integrated circuit can be BCM2035, BRF6100/6150 or MC72000 whose pins are connected by labels.

The working power supply management circuit is comprised of microprocessor M30280 and power supply management integrated circuit LM2870, LP3986 and LP3985. P7.0-P7.2 of P7 port of microprocessor circuit M30280 control the enable end EN of power supply management integrated circuit LM2870, LP3986 and LP3985. The input of LM2870 and LP3986 is connected to the positive electrode of the power supply and the input is connected to +3.3 and −3.3V power supply end of the main circuit. The input of LP3985 is connected to the positive electrode of the power supply and the output is connected is the power supply end of the main circuit.

The real-time clock circuit is comprised of microprocessor circuit M30280, real-time clock integrated MAX6902, triode switch circuit and backup power supply 2.7V lithium chargeable battery. P3.0-P3.3 of P3 port of microprocessor circuit M30280 are connected to serial clock end SCLK, serial data output DOUT, serial data input DIN, chip selection end CS of MAX6902 respectively. The negative electrode of diode D1 in diode switch circuit is connected to the +3.3V power supply end of the main circuit and the positive electrode is connected to the power supply end of MAX6902. Diode D2 is parallel connection with a current limiting resistor, its negative electrode is connected to the positive electrode of the backup power supply 2.7V lithium chargeable battery and its positive electrode is connected to the power supply of MAX6902.

The image liquid crystal circuit is comprised of microprocessor circuit M30280, liquid crystal drive integrated circuit ST7541 and matched color liquid crystal display. P0.1-P0.7 of P0 port of microprocessor circuit M30280 are connected to the data lines D0-D7 of ST7541 respectively. P7.3-P7.6 of P0 port of M30280 are connected to the chip selection CS, reset end RES, reading end RD and writing end WR of ST7541 respectively.

The mechanical vibrant circuit is comprised of microprocessor circuit M30280, driver triode MDC3105 and vibrant motor P-2511. P10.0 of P10 port of microprocessor circuit M30280 is connected to the base pole of MDC3105 via a current limiting resistor. The emitter of MDC3105 is connected to ground. One end of vibrant motor P-2511 is connected to the collector of MDC3105 and the other end is connected to +3.3V power supply end of the main circuit.

The buzzer circuit is comprised of microprocessor circuit M30280, drive triode 9012 and buzzer. P10.1 of P10 port of microprocessor circuit M30280 is connected to the base pole of 9012 via a current limiting resistor. The collector of 9012 is connected to +3.3V power supply end of the main circuit. One end of buzzer is connected to the emitter of 9012 and the other end is connected to ground.

The USB interface circuit is comprised of microprocessor circuit M30280 and USB module PDIUSBD12. P0.0-P0.7 of P0 port of microprocessor circuit M30280 are connected to D0-D7 of PDIUSBD12. P9.0-P9.5 of P9 port of M30280 are connected to the chip selection USBCS, interruption control end USBINT, reset end RESET, writing end WR, reading end RD and A0 end of PDIUSBD12. The serial communication ports D−, D+ of PDIUSBD12 are connected to the USB port of the exterior device.

The integrated circuit of the remote mobile monitoring device as stated in example 1 of this invention applies low-consumption CMOS integrated circuit fully. The working power supply voltage is ±3.3V and it applies 3.7V 800 mA lithium battery whose working time can be more than 48 hours continuously.

The working principle in Example 1 about this invention is as follows. The microprocessor circuit controls electrophysiological signal sampling processing circuit to sample analog signal of electrocardio, blood pressure and breath and commands the calibration voltage signal circuit to send calibration voltage signal. The A/D modulus converter inside the microprocessor converts the electrophysiological analog signal to digital signal. Application as stated analyses and processes the digital signal according to the calibration voltage and gain, and sends it into data storage circuit for storage. The microprocessor control data storage circuit stores different data of remote mobile monitoring devices as stated by address. The microprocessor circuit will alarm when finding pathological exception event and meanwhile put exception event data and recent relative event data into package by time sequence, power on wireless network interface circuit to access the exterior network terminal interface, build wireless dual-direction data communication link to access WAN, send event data package into the remote electrophysiological data monitoring server, and receive and execute the control command sent from the server and process medical advice.

The calibration voltage signal circuit as stated in example 1 of this invention sends calibration voltage signal in control of the microprocessor circuit, calibrates the ECG waveform QRS wave package and the range of ST of the monitoring record, and supplies to application as stated as the benchmark of self-adaptive analysis computing.

Data storage circuit as stated in example 1 of this invention includes the word base storage address, setting information storage area address, exception electrophysiological data storage area address and sequent electrophysiological data storage area address in control of application addressing as stated and meanwhile controls capacity of different storage area. Different data of remote mobile monitoring device as stated is stored in different storage areas. The data storage circuit reads, writes, modifies and cancels the corresponding area by application command and address as stated.

The wireless network interface circuit as stated in example 1 of this invention uses the international common 2.4 G Hz frequency. The wireless communication distance is 0-100 m. It has in-built TCP/IP protocol, PPP protocol, BlueTooth protocol and address code Pin for user individual identity. The matched exterior network terminal interface includes but is not limited to mobile Internet, LAN, ADSL, VDSL, ISDN, DDN, CAN communication network, electricity power communication network terminal interface to build dual-direction communication link, which has functions of automatic correction and retransmission and 79 hopping frequency points. The function of automatic hopping frequency can regulate data communication channel and cancel conflict of the same frequency or the same kind of devices to improve the reliability of data communication. The wireless network interface circuit is in the state of dormancy when not sending data. When the microprocessor circuit sends data, it will wake up the wireless network interface circuit to work.

The emergent calling circuit as stated in example 1 of this invention supplies the emergent calling triggering signal. When checking that there is an emergent calling triggering signal, the microprocessor circuit will control the wireless network interface circuit to operate, access to WAN and the SMSC via the exterior network terminal interface and send help information to the setting receiving terminal.

The working power supply management circuit as stated in example 1 of this invention supplies electricity for different module circuits. The microprocessor circuit controls three enable ends EN of power supply management circuit, and supplies steady +3.3V, −3.3 and +2.5V operating power supply according to requirements.

The real-time clock circuit as stated in example 1 of this invention supplies calendar and real time 24-hour clock for application as stated. Application reads date and time of the real-time clock circuit, and notes date and time for signal sampling storage, different event data and different operating information data. When the power supply of the main circuit supplies electricity for the real-time clock circuit, it will charge 2.7V lithium chargeable battery of the backup power supply. When the main circuit is in the state of power cut, the 2.7V lithium chargeable battery will supply electricity for the clock circuit separately.

The image liquid crystal circuit as stated in example 1 of this invention presents the scrolling display or freezing display of electrocardio, blood pressure, breath waveform and different images symbols and different language words in control of microprocessor circuit.

The mechanical vibrant circuit and buzzer circuit as stated in example 1 of this invention supplier mechanical vibration and sound for event alarming. The microprocessor circuit controls the base pole of drive triode in the mechanical vibration circuit and buzzer circuit respectively. The power supply powers on when in the state of high level and sends mechanical vibration and sound.

The SUB interface circuit and the USB interface connection of exterior devices as stated in example 1 of this invention is used to transmit and download electrophysiological data of continuous monitoring record to exterior devices for remote mobile monitoring devices as stated. The USB interface circuit can also achieve data information exchange and network data communication with exterior devices in control of the microprocessor circuit. The exterior devices include but are not limited to PC and network terminal devices with USB interface.

Example 2 this invention presents a WAN-based electrophysiological data remote mobile monitoring method including application. Application as stated controls self-adaptive analysis computing, exception event warning and alarming privilege graded setting, event data package combination, network data communication, data storage circuit area management, safety information data storage management and remote emergent calling of the remote mobile monitoring devices. It also includes the following steps:

step1: application as stated computes the current electrophysiological data according to the calibration voltage and gain sampling to obtain the initial data. If application determines that the initial data is in the setting range of threshold, it is used as the initial value of this monitoring to start monitoring analysis computing. If the initial value reaches to the setting threshold value, application as stated will set the initial value flag and store it. Set the upper limit or lower limit self-adaptively. This initial value is used as the initial value of this monitoring to start monitoring analysis computing. When the monitoring data reaches to the self-adaptive threshold value, application as stated will set the exception electrophysiological event flag and send data flag. If the initial value exceeds the setting threshold value, application as stated will set the exception electrophysiological event flag and send data flag.

step2: application as stated sets different level alarm flags according to different kinds of exception event flags as stated and set the forewarning privilege of remote mobile monitoring devices as stated including first-level warning privilege, second-level warning privilege and third-level warning privilege. When the warning flag as stated is set, the relative command circuit performs the operation of alarming or forewarning.

step3: application as stated arranges forward 6 sixty-minute intervals and obtains event data records relating to this event in the 6 intervals to compose an event data package by time sequence. When the number of intervals is less than 6, get the maximum time.

step4: application as stated commands the wireless network interface circuit to power on according to the sending data flag. Use the BlueTooth protocol to send the searching command. After the exterior network terminal interface responses in valid distance, the wireless network interface circuit sends an individual identity address code Pin to check match. Build wireless dual-direction digital communication link. Application as stated sends the recognition command to judge whether the exterior network is mobile Internet or cable network.

step5: if application as stated determines that the exterior network is mobile Internet, then read the fixed IP address of remote electrophysiological data monitoring server and call TCP/IP protocol and PPP protocol. If it is cable network, application as stated reads the fixed IP address of remote electrophysiological data monitoring server, calls the cable network control command, controls the wireless network interface circuit to connect the mobile Internet or cable network, performs network digital communication with remote electrophysiological data monitoring server, sends event data packages or data information, receives the control command, analysis result and processing medical advice sent from the server and responses to execute the control command.

step6: application as stated controls wireless network interface circuit to enter into the online connection holding state (Hold). Stop data transmission and hold online connection. When application as stated or remote electrophysiological data monitoring server send activation signal, recover digital communication immediately.

step7: data memory circuit as stated is divided into word base storage area, setting information storage area, safety information storage area, exception electrophysiological data storage area, continuous electrophysiological data storage area according to application addressing as stated. Execute the operation of reading, writing, modification and cancellation according to the corresponding areas of the application commands and address as sated. Set the safe information storage area for cyclic record storage which can not been cancelled artificially and the cyclic record period can be set with flexibility.

step8: when application as stated receives setting information data from the remote mobile monitoring devices as stated, it will send the writing command to the data storage circuit and set address for data to store it in the setting information storage area.

step9: when application as stated receives operating information data from the remote mobile monitoring devices as stated, it will send the writing command to the data storage circuit and set address for data to store it in the sate information storage area.

Step10: when application as stated receives emergent calling triggering signal, set the emergent calling flag and send data flag. Read SP code digital mobile phone number or MMS address and help information, control the wireless network interface circuit to access the connection SMSC of mobile network terminal interface and send help information to the predetermined receiving terminal. If application as stated does not receive "receive" information sent from the receiving terminal, read the fixed IP address and help information of the binding remote electrophysiological data monitoring server, control the wireless network interface circuit to access WAN, send help information to the remote electrophysiological data monitoring server, receive the "receive" information sent from the receiving terminal and terminate cyclic calling.

We will introduce details of the working flow of this invention below. Refer to FIG. 2, FIG. 3, FIG. 4, FIG. 5, FIG. 6, FIG. 7, FIG. 8, FIG. 9, and FIG. 10 for the hardware principle figure and software flow chart.

As show in FIG. 2 and FIG. 3, the 1-3 analog signal channels of electrophysiological signal sampling circuit as stated in this invention is a synchronization three-lead ECG channel. The lead system can be CMVI+CMV3+CMV5 or CMV2+CMV5+Mavf of hematal monitoring lead system. The front-end amplification circuit with 1-3 analog signal channels uses high precision meter amplifier with high suppression ratio of common mode to lower disturb of the common mode. The ECG analog signal is divided into two channels after amplified, one of which goes into the programmable control gain amplification circuit and band pass filter circuit by pacing pulse suppression circuit and blocking circuit to amplify the analog signal to filter disturb of high/low frequency, and then into the A/D modulus converter for modulus conversion. The function of pacing pulse circuit is to lower stretching pulse to reduce the effect of pacing pulse to ECG signal. The function of blocking circuit is to filter the DC voltage and DC polarization voltage and couple the ECG analog signal to the lower level without distortion. The function of programmable control gain amplification circuit is to regulate the amplifier times by the ECG signal. The broadband of band pass filter circuit is 0.05 Hz-100 Hz for functions such as filtering high-frequency myoelectricity disturb and benchmark line shifting and supplies high-quality original signal. The ECG signal of the other channel goes into the R ware trigger circuit, supplies to R wave time sequence for microprocessor analysis program by the hardware circuit check QRS wave group and analyses ECG wave group with software program. The output of calibration voltage signal circuit is connected to output of blocking circuit to avoid effect each other. When P1.2 of the microprocessor circuit is high level, the calibration voltage signal circuit will generate benchmark voltage automatically needed for ECG data computing and analysis and mark it in the front of each frame of ECG image by the mode of rectangular wave. The 4 and 5 channels are the blood pressure signal channel and the breath signal channel, which is comprised of band pass filter, limitr and reshaper. The sensor can use the existing portable dynamical blood pressure meter and constant current source thorax impedance breath monitoring meter. Two analog signal output are connected to the input of the 4-5 analog signal channel. Filter high/low frequency disturb by band pass filter circuit and enter into A/D modulus converter for conversion after amplitude limiting and shaping. The 10-bit A/D modulus converter inside the microprocessor M30280 samples and converts analog signal of five channels synchronistically. The sampling precision is up to 3

μv to meet requirements for electrophysiological signal monitoring analysis. Meanwhile it can monitor and sample data of electrocardio, blood pressure, breath physiology. The 4 and 5 channels can been shut down artificially. When 4 and 5 channels are shut down, application as stated will stop sampling and processing signal of these two channels.

As showed in FIG. 4-FIG. 11, the microprocessor as stated in this invention is core of remote mobile monitoring devices as stated, which has application inside FlashROM for control of machine running and different module circuits. Application as stated includes these following application such as main program, electrophysiological data analysis subprogram, smart diagnosis subprogram, wireless dual-direction communication control subprogram, control command processing subprogram, emergent calling subprogram, event forewarning and alarming subprogram. When the microprocessor runs, application as stated will first initialize for self-test to check the state of different modulus circuit and the state of the exterior network terminal interface in valid distance. After self-test, sample electrophysiological analog signal for A/D, modulus conversion, use common band pass digital filter for further filtering myoelectricity noise disturb, benchmark line shifting and power frequency disturb to obtain high-quality electrophysiological digital signal which is stored in data storage circuit after analysis and processing by classification.

Figure 6:
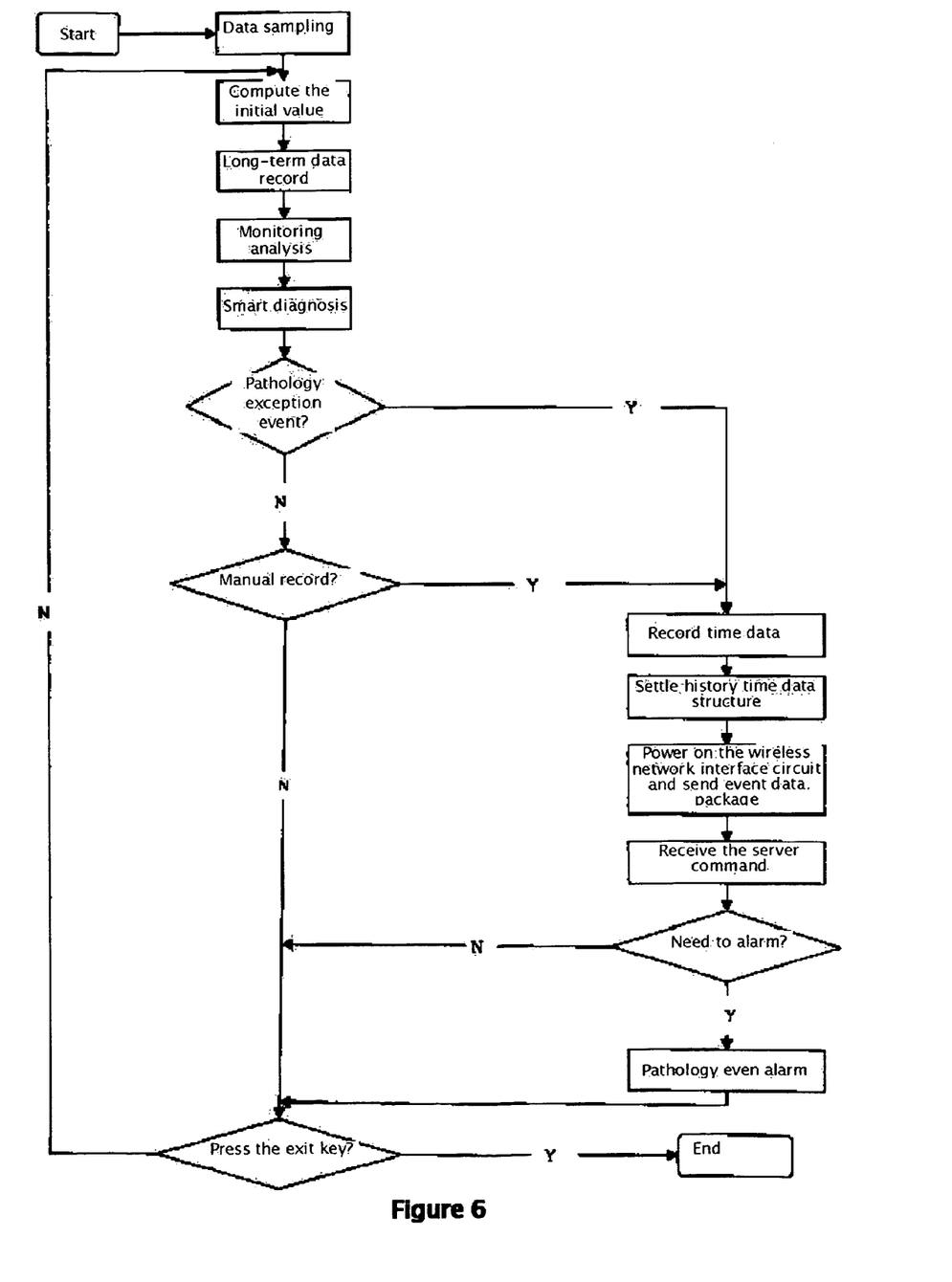
FIG. 6, subprogram flow chart for electrophysiological data analysis.

This invention presents an electrophysiological data self-adaptive analysis computing method which can forewarn to electrophysiological data which can endanger person safety. Analysis for ECG data mainly includes arrhythmia and ST range change. Analysis for blood pressure data is mainly to compute the blood change trend and difference of pulse according to 24-hour blood pressure change data, and build a 24-hour blood pressure trend figure. Analysis for breath data is mainly to compute frequency of breath, pacing and time of pause according to breath frequency change to build a 24-hour blood pressure trend figure.

We should also consider exception change of electrophysiological data of partial users and physiology change of electrophysiological data of users in normal life. The purpose of self-adaptive analysis computing as stated is to monitor dynamical change of electrophysiological data with clinic meaning. Application as stated computes main parameters such as R-R interval, time limiting of QRS wave group, range value of ST, systolic pressure, diastolic pressure and breath period, according to time sequence supplied by hardware circuit R wave trigger and calibration voltage range value supplied by calibration voltage signal circuit. Programmable control microprocessor circuit as stated first samples and computes the existing user electrophysiological data to obtain initial data. If initial data is in the range of setting threshold value judged by application as stated, initial data will be considered as the initial value of this monitoring to start checking and computing. If initial data reaches to the setting threshold value, application as stated will mark initial data as the initial value and store. Regulate the upper limit or lower limit self-adaptively. This initial data will be considered as the initial value of this monitoring to analyse and compute. When monitoring data continues to change and reaches to the self-adaptive threshold value, application as stated will response and forewarn. If initial data exceeds the setting threshold value, application will mark pathology exception event and send data flag, meanwhile generate three-grade warning flag and forewarn.

Considering ECG signal data self-adaptive analysis and computing as an example, if time of user initial data cardiac arrest has already reached to 3 seconds of setting threshold value, application will set initial value event flag and store and regulate the setting threshold to 3.3 seconds self-adaptively. When time of cardiac arrest reaches to 3.3 of self-adaptive threshold value, set pathology exception event flag and send data flag, meanwhile set three-level warning flag and control the image liquid crystal circuit to flicker and word forewarning. Application packages this event data and recent relative event data according to pathology exception event flag and sending data flag, powers on wireless network interface circuit to access to the exterior network and sends event data package to remote electrophysiological data monitoring server for processing. Application as stated receives and executes the control command sent from remote electrophysiological data monitoring server to determine whether to alarm for pathology exception event. The advantage of self-adaptive analysis and computing method of this invention is that it can monitor and catch electrophysiological data dynamical change and exception change with clinic meaning. Avoid repeatable numerous operating of setting and analyzing the threshold value in user terminal. So it is convenient for users and solves problems in the existing technology.

This invention presents a method of data storage circuit area management and safety information data storage management. Application addressing control data storage circuit as stated is divided into five data storage areas and meanwhile controls capacity of different storage areas. Application as stated controls operations of reading, writing, modification and cancellation of five control data storage. The word base storage area mainly stores different parameter information data set by user. The setting information data can be word, symbol, character, digital, image and combination, including but not limited to fixed IP address, SP code and digital mobile telephone number, MMS address, user name and password and help information of binding remote electrophysiological data monitoring server; the exception electrophysiological data storage mainly stores exception event electrophysiological data and manual operation record data; the continuous electrophysiological data storage area mainly stores 24-hour continuous monitoring electrophysiological data, in which it can store maximum 48-hour continuous electrophysiological data; the safety information storage area mainly stores user operation information data, in which application as stated sets cyclic record storage which can not be cancelled artificially. And the cyclic record period can be regulated. Operation information data includes but is not limited to ON/OFF time, alarming reason and time, mode of sending data and sending time, content and time of response control command data, content and time of receiving medical advice, emergent calling triggering event time and response time. The data storage circuit records and stores sudden emergent electrophysiological data and continuous electrophysiological data, meanwhile stores safety information data as medical care evidence and extends its function and application of data storage circuit.

Figure 5:
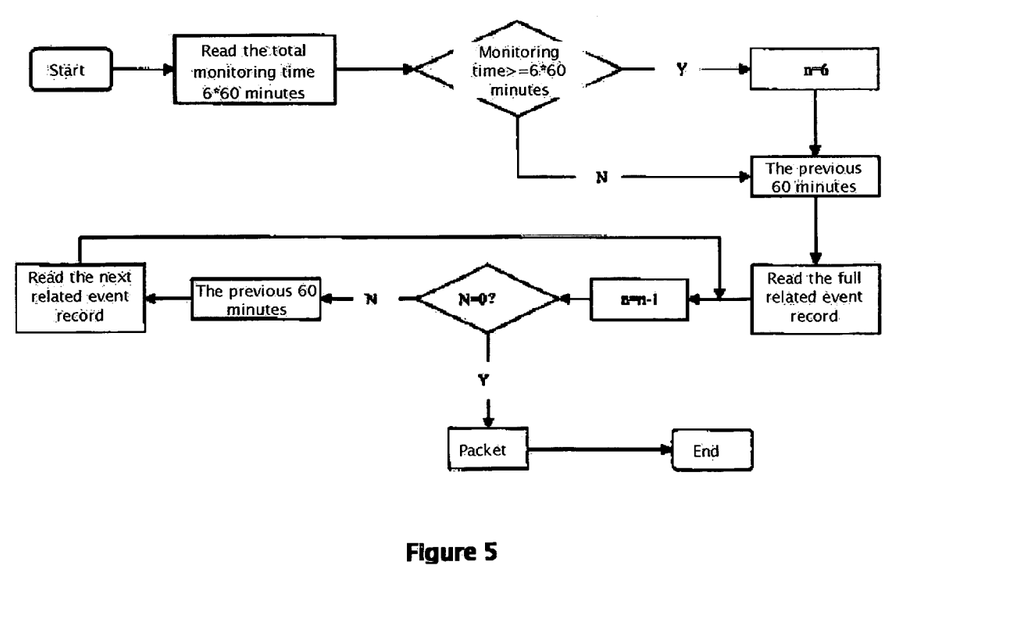
FIG. 5, subprogram flow chart for event data package processing.

This invention presents an event data package combination method. When application as stated receives exception event flag and sends data flag, it arranges forward 6 sixty-minute intervals according to occurrence time of this exception event flag, namely Tn, Tn-1, Tn-2, Tn-3, Tn-4, Tn-5. Application as stated sets Tn time interval and stores it together with event record data relating to this event into data package. Search one relating event record data to store into data package in each interval ahead of Tn time interval and compose an event data package by time sequence. The time interval is less than 6. Get the maximum time. The event data package combination solves the problem of multi sending or only sending data in some time interval needed in the existing technology.

Figure 7:
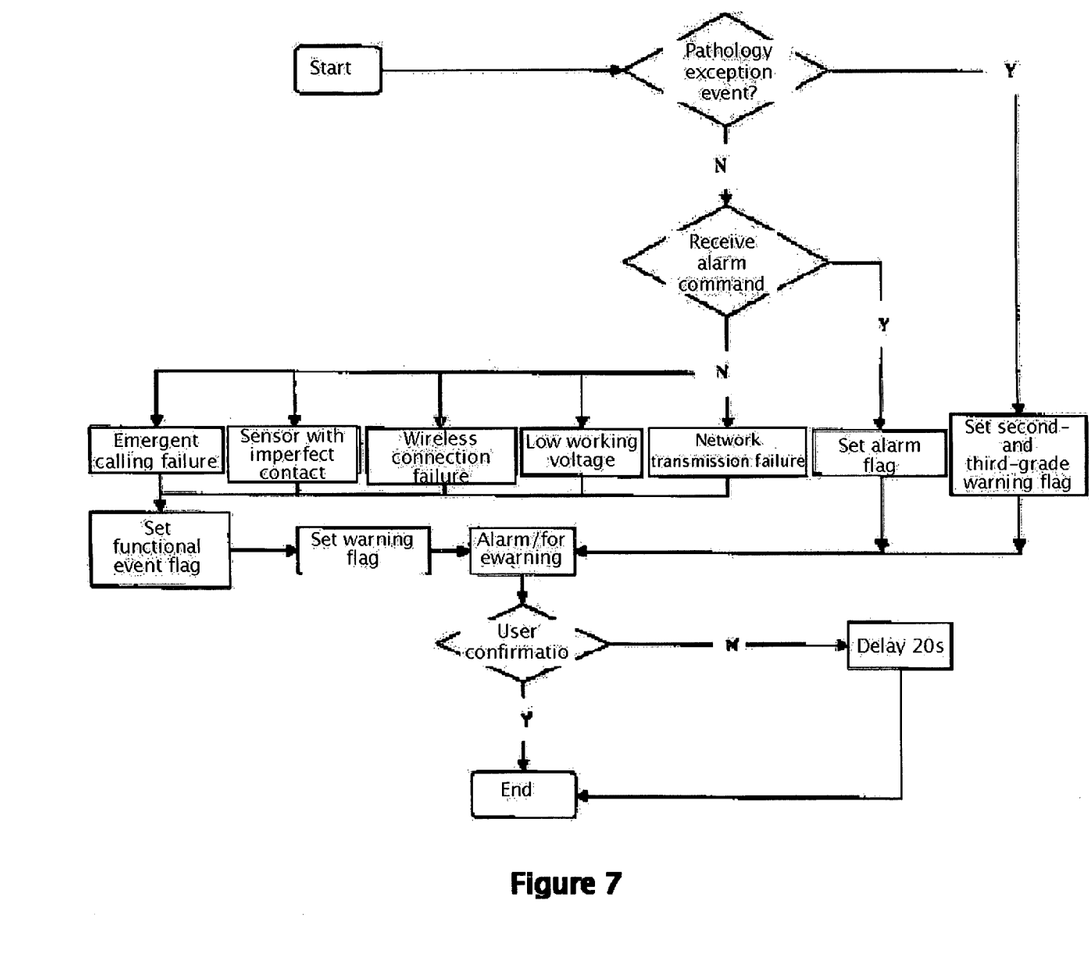
FIG. 7, subprogram flow chart for event forewarning and alarming.
Figure 8:
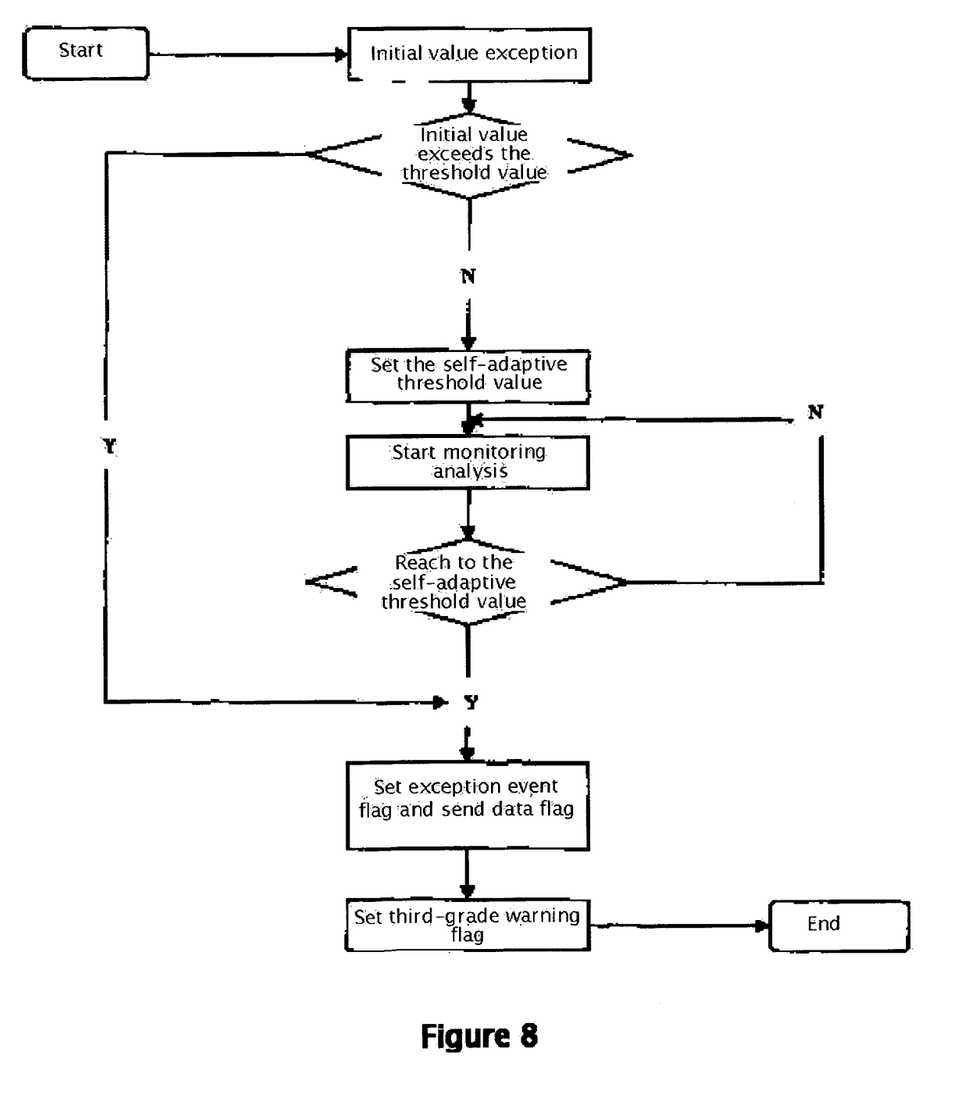
FIG. 8, subprogram flow chart for smart diagnosis.

This invention presents an exception event warning and alarming privilege grade setting method. Application as stated sets warning flag for the exception event grade. The setting microprocessor circuit has first-grade warning privilege, second-grade privilege and third-grade warning privilege and controls forewarning and alarming of remote mobile monitoring devices as stated. One-grade warning is mainly a functional event, including but not limited to events such as sensor dropping, insufficient working voltage, interconnection signal interruption, interconnection sending failure, wireless connection failure and emergent calling failure. When application finds functional event, it will set functional event flag, set first-grade warning flag according to functional event flag and command related circuit to alarm in the mode of vibration, sound and word. Terminate alarming after user confirmation. Second-grade warning is mainly manual record triggering event and pathology exception event which reaches to the setting threshold value, including arrhythmia and ST change, blood pressure change and breathing rhythm change when reaching to the setting threshold value. When application finds manual record event or pathology exception event which reaches to the setting threshold value, set the exception flag and send data flag, and set second-grade warning flag according to exception event flag. The third-grade warning is mainly pathology exception event which exceeds the setting threshold and reaches to the self-adaptive threshold value, including serious arrhythmia, acute ST change, fierce blood pressure and sudden breath stop. Application as stated commands related circuit to flicker and forewarn by word according to second-grade warning flag and third-grade warning flag, prompts user that there is exception sent to the remote electrophysiological data monitoring server, meanwhile receives and executes the control common sent from the server and determines whether to alarm according to control command. So it solves the problem of pathology exception event alarming.

Figure 9:
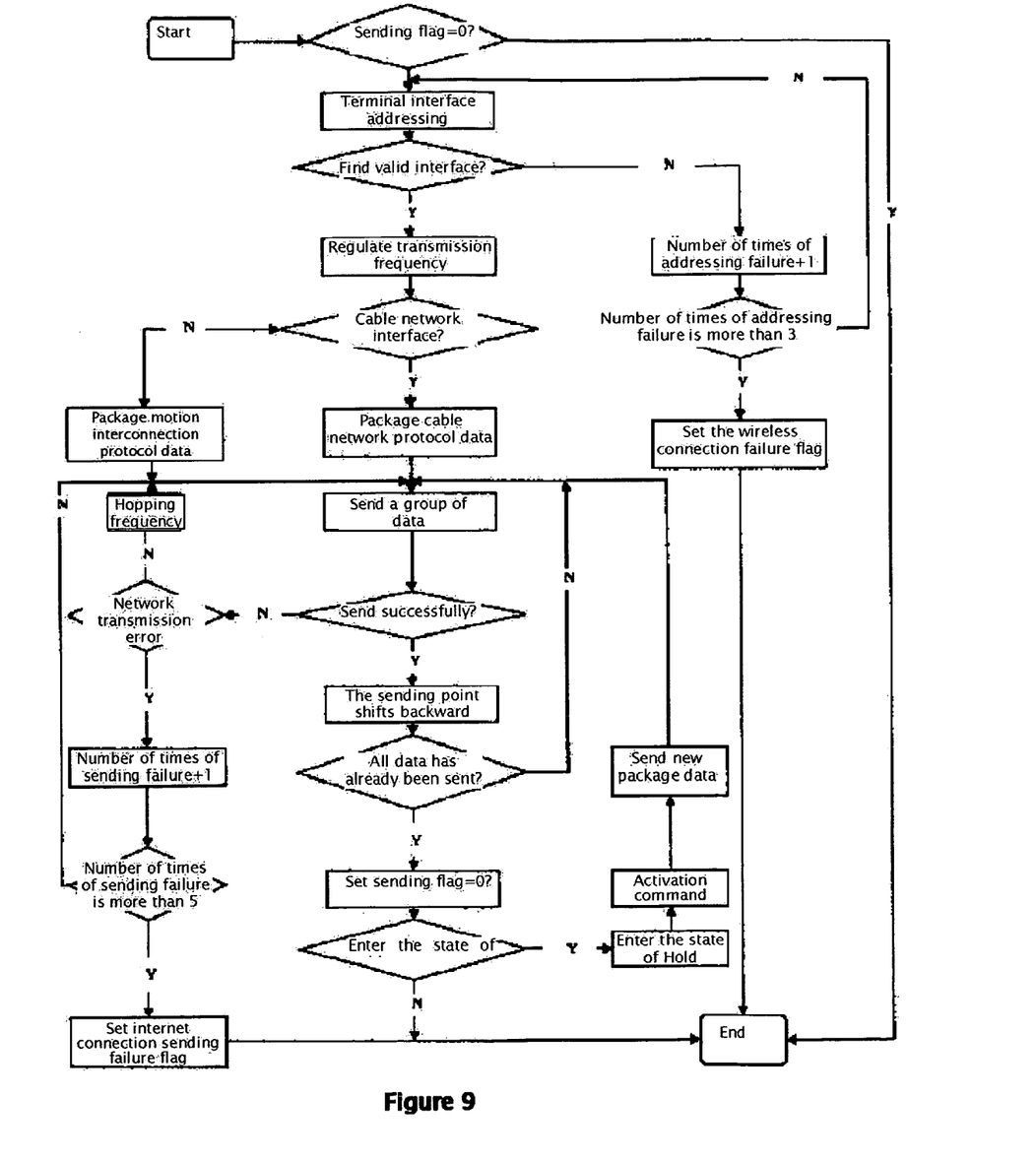
FIG. 9, subprogram flow chart for wireless dual-direction communication control.
Figure 10:
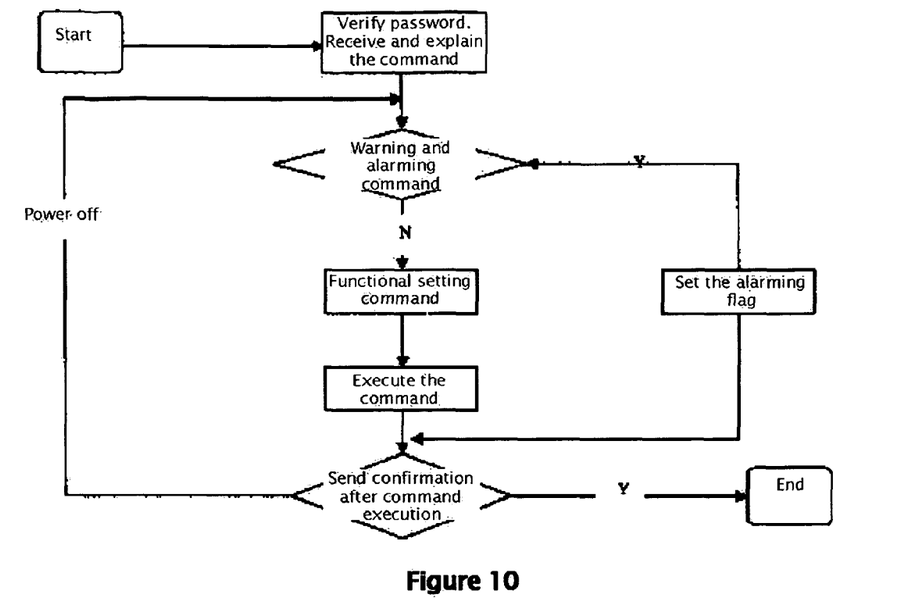
FIG. 10, subprogram flow chart for control command processing.

This invention presents a method of network digital communication of electrophysiological data. When application receives the sending data flag, it will wake up the wireless network interface circuit, call the BlueTooth protocol to send searching command. After the exterior network terminal interface responses in valid distance, the wireless network interface circuit sends personal identity address code Pin authority match and builds a wireless dual-direction digital communication link with the exterior network terminal interface. The wireless network interface circuit sends identity command to the exterior network and judges whether the exterior network is mobile Internet or cable network. If it is mobile Internet, application as stated reads the fixed IP address of remote electrophysiological data monitoring server and call TCP/IP protocol and PPP protocol. The wireless network interface circuit builds a dual-direction digital communication link with mobile Internet and sends event data package to the remote electrophysiological data monitoring server. If it is cable network, application as stated reads the fixed IP address of the remote electrophysiological data monitoring server, calls the cable network control command. The wireless network interface circuit builds a dual-direction digital communication link with cable network and sends event data package to the remote electrophysiological data monitoring server. The wireless network interface circuit receives the control command, diagnosis verdict and medical advice sent from the remote electrophysiological data monitoring server. Then the microprocessor circuit processes this information after demodulation. The microprocessor circuit responses and executes the control command, and sends the executing result to the remote electrophysiological data monitoring server. The control command as stated can be standard operation command and data, or self-customized command and data, including but not limited to password verification command, internal information obtain command, function setting command and pathology exception event alarming command. The wireless network interface circuit monitors the sending data automatically and correct, and judges whether it is wireless transmission error or network transmission error. If it is wireless transmission error, execute operation of hopping frequency and resend. If the times of network transmission errors are more than 5, set the "interconnection transmission failure" flag.

In control of application as stated, the wireless network interface circuit has the function of continuous online keeping (Hold). The wireless network interface circuit terminates data transmission to lower power consumption and keep online connection in the state of Hold. When the microprocessor circuit or remote electrophysiological data monitoring server sends activation signal, recover digital communication immediately. Application as stated controls the switch of the wireless network interface circuit between inter network. If the number of failure of searching the exterior network terminal interface is 5, then set the "wireless connection failure" flag and send alarming to prompt users. The exterior network terminal interface of wireless network interface circuit includes and is not limited to mobile Internet, LAN, ADSL, VDSL, ISDN, CAN communication network and electricity power communication terminal interface. User can access to the exterior network terminal interface wirelessly nearby to connect to WAN for network digital communication. It can access to Internet in motion and switch between inter network for roaming interconnection. It can keep online connection to compensate disadvantages in the existing technology.

Because the wireless network interface in this invention uses the international universal BlueTooth protocol specification and network protocol, the digital mobile telephone BlueTooth wireless interface of mobile Internet terminal in the exterior network terminal interface and BlueTooth wireless access devices of cable network terminal uses the existing technology. We do not give more details.

Figure 11:
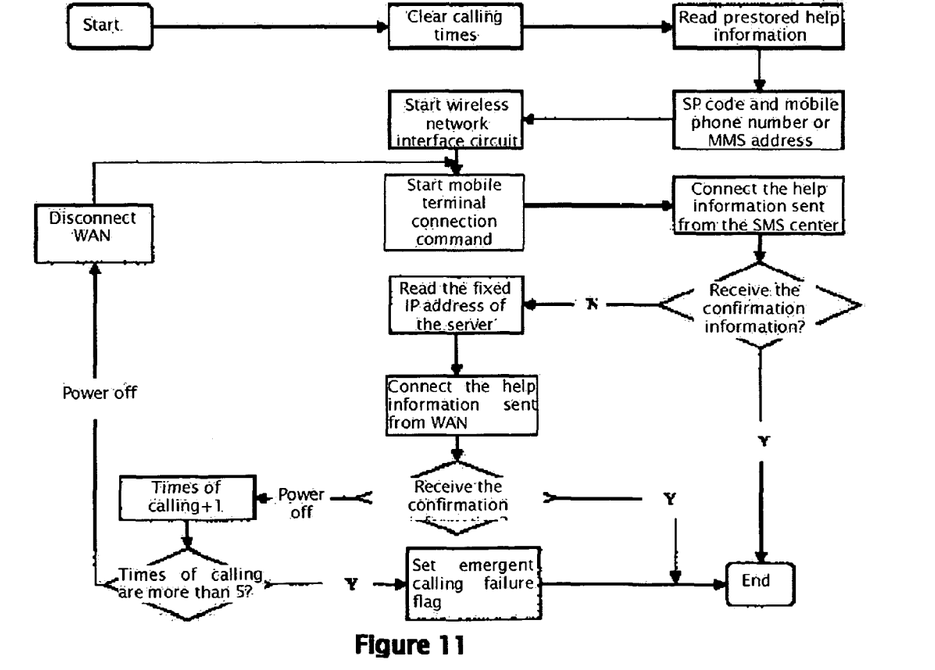
FIG. 11, subprogram flow chart for emergent calling.

This invention presents a remote emergent calling method. The emergent calling circuit sends triggering signal to the microprocessor circuit. Application as stated sets emergent calling flag and sends data signal, reads SP code, digital mobile phone number or MMS address and help information prestored in the information storage area, controls the wireless network interface circuit to access to the mobile Internet terminal interface for connecting to the SMSC, sends help information to predetermined receiving terminal and waits for "received" confirmation information sent from the terminal which can be digital mobile phone or PC/server. If not receiving "received" confirmation information sent from the terminal in ten seconds, application as stated reads the fixed IP address and help information of electrophysiological data monitoring server, controls the wireless network interface circuit to access to the exterior network interface for connecting to WAN and sends help information to the remote electrophysiological data monitoring server. Send help information cyclically. If receiving "received" confirmation information sent from the receiving terminal, stop cyclic calling and exit. If times of cyclic calling is more than 5, set the "emergent calling failure" flag and send alarming to prompt user. So it solves the problem of emergent calling help under user non-monitoring state.

The microprocessor circuit controls three enable ends EN of power supply management integrated circuit respectively. When the enable EN is high level, the power supply management circuit powers on and supplies steady +3.3V, −3.3V and +2.5V working power for different module circuits according to requirements. So it saves power and lowers power consumption.

The real-time clock circuit supplies calendar and real-time 24-hour clock. Application as stated reads data and time, and it notes date and time for signal sampling storage, different event data, different setting information data and different operation information data. When the power supply of the main circuit supplies electricity for the real-time clock circuit, it will charge the lithium chargeable battery of the backup power supply at the same time. When the power supply of the main circuit disconnects, the lithium chargeable battery will supply electricity for the real-time clock circuit separately and assure continuous operation of the real-time clock circuit.

The image liquid crystal circuit is used to show electrocardio, blood pressure, breath waveform, image symbol and word of different languages. Application as stated commands the microprocessor circuit to control the image liquid crystal circuit to present the scrolling display or freezing display of electrocardio, blood pressure, breath waveform and different images symbols and different language words as warning and forewarning in control of microprocessor circuit.

The mechanical vibrant circuit and buzzer circuit is used to supply mechanical vibration and sound for event alarming. The microprocessor controls the mechanical circuit, buzzer circuit and image liquid crystal circuit to alarm in the mode of vibration, sound and word according to first-grade warning flag. The microprocessor circuit controls the image liquid crystal circuit to forewarn in the mode of flicker and word according to two-grade and third-grade warning flag, and meanwhile sends event data package to the remote electrophysiological data monitoring server. When the microprocessor circuit receives the control command of alarming sent from the server, it controls related circuit to alarm in the mode of vibration, sound and word.

The remote mobile monitoring device as stated records equal or more than 24 hours of continuous monitoring electrophysiological data supplied to doctors for analysis. USB interface is connected to the USEB interface of the exterior device if needed. Transmit and download electrophysiological data of continuous monitoring record. In control of microprocessor circuit, the USB interface circuit can exchange data information and take network digital communication with the exterior devices which include but are not limited to PC and the network terminal devices with USB interface.

The program of this invention is written in C language. So it features good extendibility and transferability and is fit for different kinds of monolithic processors.

This invention is a new kind of individual medical care information tool with the function of network. It can monitor dynamical change of electrophysiological data automatically, access to WAN for network digital communication wirelessly, connect to Internet in motion and switch to the roaming Internet between inter network, build wireless dual-direction communication link with any styles of mobile Internet terminal interface and also judge the position where the user sends and receives information by the mobile Internet terminal interface. So it is very suitable for large number of persons for electrophysiological remote mobile monitoring.

We explain this invention in details above. Many equivalent, replaceable and corrective solutions based on this patent can derive from it. Some functions without affecting other functions in this invention can be used independently.

What is claimed is:

1. A Wide Area Network (WAN)-based remote mobile monitoring device for electrophysiological data comprising:

a microprocessor connecting and controlling functional module circuits of said remote monitoring device to make early-warning for monitoring of electrophysiological data, to save data and to establish digital communication of network;

an electrophysiological signal processor to collect electrophysiological data, said electrophysiological signal processor comprising an internal calibration voltage signal circuit to provide a benchmark calibration voltage;

a data memory circuit comprising five data storage areas storing various data of said remote mobile monitoring; said data storage areas including text storage area, setting information storage area, safety information storage area, abnormal electrophysiological data storage area, and continuous electrophysiological data storage area;

an image liquid crystal circuit displaying waveform, image symbols of electrophysiological data and texts with various languages;

a real-time clock circuit displaying date and time when the data being saved;

a wireless network interface circuit being built-in Transmission Control Protocol/Internet Protocol (TCP/IP), Point-to-Point Protocol (PPP), short-range communications, which are wirelessly able to access exterior network terminal interface to connect WAN with said digital communication of network;

an emergent calling circuit transmitting an emergent triggering signal to said microprocessor which commands said wireless network interface circuit to transmit helping request to desired receiving ends;

a power supply management circuit supplying electricity for various functional modules of said remote mobile monitoring under the control of said microprocessor;

a mechanical vibration and buzzer circuit conducting mechanical vibration and sound for alarm when warning flags being occurred under the control of said microprocessor;

a Universal Serial Bus (USB) interface circuit being utilized to exchange data between said remote mobile monitoring device and exterior devices, and to download the electrophysiological data of continuous monitoring from said remote mobile monitoring device.

2. The WAN-based remote mobile monitoring device for electrophysiological data according to claim 1, wherein said microprocessor comprising a low-power monolithic processor to connect Input/Output (I/O) port, exterior interruption source, serial communication port and internal Analog-to-Digital (A/D) analog converter to various functional modules, respectively; whose universal flash programming utility being installed with software application; said low-power monolithic processor is a monolithic processor M302280 or HD64F3847.

3. The WAN-based remote mobile monitoring device for electrophysiological data according to claim 2, wherein said internal calibration voltage signal circuit comprising a precision benchmark resource, a triode 9013, current limiting resistors, precision voltage division resistors; base of said triode 9013 being connected to P1.3 of P1 port, emitter of said triode 9013 being connected to +3.3V power supply port of main circuit, and collector of said triode 9013 being connected to ground and negative electrode of said precision benchmark resource via two said current limiting resistors, respectively; two said precision voltage division resistors being in series in which one end being connected to the negative electrode of said precision benchmark resource, another end being connected to ground and the middle end being connected to output end of a blocking circuit; at the output end, said benchmark calibration voltage being 1 mv×multiple of preamplifier stage with deviation error less than ±1%.

4. The WAN-based remote mobile monitoring device for electrophysiological data according to claim 2, wherein said storage circuit consisting of a storage microprocessor and a memory data storage device; said storage microprocessor being a storage monolithic processor which is a monolithic processor M30208; said memory data storage device is a memory card is NAND01G; P0.0-P0.7 of P0 of M30280 being connected to the data lines D0-D7 of NAND01G, respectively, and P2.2-P2.4 of P2 of M30280 being connected to chip selection end E, address locking end AL and command locking end CL of NAND01G, respectively; or said memory card is K9K1GU0B, TC58DVG02A1 FT00 or RC28F13C-150 whose pins being connected with these of said storage monolithic processor by labels.

5. The WAN-based remote mobile monitoring device for electrophysiological data according to claim 2, wherein said wireless network interface circuit comprising an interface microprocessor which is a monolithic processor M30208, a network processing circuit IP2022, and a short-range communication integrated circuit which is BlueCore313143; the series communication ports, TXD, RXD, CTS, DSR, of said processor M30280 being connected to the series communication 1 of said network processing circuit IP2022; P5.O-P5.2 of P5 port of said processor M30280 being connected to reset end, state control end PRG, sleeping control end ON/OFF, respectively; PORTSEI end, SLEEP_ENABLE end, HOST_INT end and DISCONNECT end of said network processing circuit IP2022 series communication 2 being connected to the UART_RX end, UART_TX end, UART_RTS end and UART_CTS end of said BlueCore313143, respectively; the PORTSEI end, SLEEP_ENABLE end, HOST_INT end, DISCONNECT end of IP2022 being connected to the reset end RESET, power supply control VREG_EN end, wakeup end PWR_UP disconnection end DISCONNECT_CON of said BlueCore313143; said short-range communication integrated circuit is BCM2035, BRF6100/6150 or MC72000 whose pins are connected by labels.

6. A WAN-based remote mobile monitoring method for electrophysiological data comprising the following steps operated by a software application:

step1: the calibration voltages and accumulating samplings being used to compute current electrophysiological data to obtain initial data;

if said initial data being in setting range of threshold value, which is set as initial value of current monitoring; if said initial value reaching setting threshold value, said initial value being flagged and saved, the upper limit or lower limit of threshold value be automatically reset; the initial data being utilized as the initial value of current monitoring to launch the analysis and computation for the monitoring; when monitoring value reaching to said reset limits of threshold value, abnormal electrophysiological event being flagged and transmitted;

if said initial data exceeding said setting range of threshold value, the abnormal electrophysiological event being flagged and transmitted;

step2: different levels of warning being set and represented by different flags based on the different electrophysiological abnormal signals; forewarning privileges of said remote mobile monitoring device being set as first-level warning privilege, second-level warning privilege and third-level warning privilege; said mechanical vibration buzzer circuit being used for the operation of alarming or forewarning when warning flag being received;

step3: retrieving the monitoring data being saved prior to the abnormal electrophysiological event occurred; an event data package being created by six event data related to current monitoring event in sixty-minute interval and corresponded time when the event data being saved; the maximum event data being retrieved if the saved intervals being less than six;

step4: when warning flag being detected, said wireless network interface circuit to initiate said short-range communication protocol to send searching command; after exterior network terminal interface being responded in a valid distance, said wireless network interface circuit transmitting an individual identity address code Pin for pairing, then wireless dual-direction digital communication being linked; a recognition command be sent to determine whether said exterior network being either a mobile Internet or cable network;

step5: if the exterior network being detected as mobile Internet, the permanent IP address of remote electrophysiological data monitoring server being read, and TCP/IP protocol and PPP protocol being performed; if the exterior network being detected as a cable network, the permanent IP address of remote electrophysiological data monitoring server being read, the cable network control command being trigged to control said wireless network interface circuit to connect the mobile Internet and cable network, to perform said digital communication of network with said remote electrophysiological data monitoring server, to transmit said event data packages or data information, to receive control command, to analyze results, to process notes sent from doctors, and to execute the control command;

step6: said wireless network interface circuit being commanded by said software application to enter into the online connection holding state (Hold), to cease data transmission and to hold online connection; the digital communication of network being able be recovered immediately once activation signal being sent by said remote electrophysiological data monitoring server;

step7: the operation of reading, writing, modification and deletion of data is performed in the corresponding areas of said data memory circuit; the cyclic record in safety information storage area being unable to be deleted and the cyclic record period is reset;

step8: when the setting information data being received from said remote mobile monitoring devices, writing commands being sent to the data memory circuit, the setting information data being saved in addressed in the setting information storage area;

step9: when operating information data being received from said remote mobile monitoring devices, said software application sending writing commands to said data memory circuit, said operating information data being saved in addressed in the safety information storage area;

step10: when the emergent calling signal be triggered, the emergent calling being flagged and transmitted, said software application is read SP code digital mobile phone number or Multimedia Messaging Service (MMS) address and helping information, to control said wireless network interface circuit to connect Short Message Service Center (SMSC) of mobile network terminal interface and to send helping information to the desired receiving ends; if said software application not receiving "received" information being sent from the desired receiving ends in ten seconds, said software application to read permanent IP address and helping information of binding remote electrophysiological data monitoring server, to command said wireless network interface circuit to access WAN, to send helping information to said remote electrophysiological data monitoring server; when said software application receiving "received" information being sent from said desired receiving ends, and the cyclic calling being terminated.

7. The WAN-based remote mobile monitoring method for electrophysiological data according to claim 6, wherein said remote mobile monitoring device is able to access WAN wirelessly, to enter into online connection holding state (Hold) under control of said software application, to terminate data transmission and hold online connection; said digital communication of network is recovered immediately once said software application or said remote electrophysiological data monitoring server issuing activation signal.

8. The WAN-based remote mobile monitoring method for electrophysiological data according to claim 6, wherein said remote mobile monitoring device is able to access said wireless network interface circuit, to connect said SMSC under control of said software application, to transmit helping information to the desired receiving ends via SMS or MMS and is receive information being sent from the desired receiving ends.

9. The WAN-based remote mobile monitoring method for electrophysiological data according to claim 6, wherein said wireless network interface circuit is able to receive the control command which is be able to being standard operating command and data, or user-defined command and data including requesting password command, function setting command, internal information command and warning command of abnormal pathological event.

10. The WAN-based remote mobile monitoring method for electrophysiological data according to claim 6, wherein said setting information is able to be texts, symbols, characters, digitals, images and mixed objects, and to be permanent IP address, SP code, digital mobile phone number, MMS address, username and password and helping information of said binding remote electrophysiological data monitoring server.

11. The WAN-based remote mobile monitoring method for electrophysiological data according to claim 6, wherein said operating information data including on-off times and time, warning contents and time, manner of sending data and time, control command data content and time, receiving medical advice content and time, emergent calling triggering event and time, and responding/answering and time.

* * * * *